US010559072B2

(12) United States Patent
Makino

(10) Patent No.: US 10,559,072 B2
(45) Date of Patent: Feb. 11, 2020

(54) IMAGE DETECTION DEVICE AND IMAGE DETECTION SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 15/738,226

(22) PCT Filed: Jun. 1, 2016

(86) PCT No.: PCT/JP2016/002655
§ 371 (c)(1),
(2) Date: Dec. 20, 2017

(87) PCT Pub. No.: WO2016/208125
PCT Pub. Date: Dec. 29, 2016

(65) Prior Publication Data
US 2018/0174283 A1 Jun. 21, 2018

(30) Foreign Application Priority Data
Jun. 23, 2015 (JP) .................. 2015-125968

(51) Int. Cl.
G06T 5/00 (2006.01)
G06T 7/00 (2017.01)

(52) U.S. Cl.
CPC ............ *G06T 5/009* (2013.01); *G06T 7/97* (2017.01); *G06T 2207/10152* (2013.01)

(58) Field of Classification Search
USPC ..................................... 382/274
See application file for complete search history.

(56) References Cited

U.S. PATENT DOCUMENTS 5,576,827 A * 11/1996 Strickland .......... G01N 15/0211
356/336
9,183,427 B2 11/2015 Chiba
(Continued)

FOREIGN PATENT DOCUMENTS

JP H04-241832 A 8/1992
JP H06-225854 A 8/1994
(Continued)

OTHER PUBLICATIONS

JP, 2015-125968 (2017-006433), Jun. 23, 2015 (Jan. 12, 2017), Takao Makino (Hoya Corp.).
(Continued)

Primary Examiner — Jerome Grant, II
(74) Attorney, Agent, or Firm — Kilpatrick Townsend & Stockton LLP

(57) ABSTRACT

An image detection device executing a detection process for images of a subject obtained by illuminating cyclically the subject with light having different spectral properties and capturing the subject at timings synchronizing with illuminating cycles of the light, the image detection device comprising a shift vector detection means that detects a shift vector of the subject based on a comparison result between an image of the subject captured at a current cycle and an image of the subject which is captured at a past cycle and is illuminated with the light having a same spectral property as that of the light illuminated at the current cycle.

20 Claims, 5 Drawing Sheets

(56) References Cited

U.S. PATENT DOCUMENTS

| | | | |
|---|---|---|---|
| 2008/0111773 A1* | 5/2008 | Tsuge | G09G 3/3241 |
| | | | 345/76 |
| 2009/0091554 A1* | 4/2009 | Keam | G06F 3/0421 |
| | | | 345/175 |
| 2014/0185907 A1 | 7/2014 | Chiba | |
| 2014/0376817 A1 | 12/2014 | Yaguchi | |
| 2015/0030254 A1 | 1/2015 | Yaguchi | |
| 2016/0202164 A1* | 7/2016 | Trainer | G01N 15/0211 |
| | | | 356/336 |
| 2016/0284120 A1* | 9/2016 | Hasselgren | G06T 1/60 |

FOREIGN PATENT DOCUMENTS

| | | |
|---|---|---|
| JP | 2001-136540 A | 5/2001 |
| JP | 2013-222383 A | 10/2013 |
| JP | 2017-006433 A | 1/2017 |
| WO | WO-2013/047054 A1 | 4/2013 |
| WO | WO-2016/208125 A1 | 12/2016 |

OTHER PUBLICATIONS

PCT, PCT/JP2016/002655 (WO 2016/208125), Jun. 1, 2016 (Dec. 29, 2016), Takao Makino (Hoya Corp.).
PCT/JP2016/002655, International Preliminary Report on Patentability, dated Dec. 26, 2017, 8 pages.
International Search Report and Written Opinion dated Sep. 6, 2016 by the International Searching Authority for Patent Application No. PCT/JP2016/002655, which was filed on Jun. 1, 2016 and published as WO 2016/208125 dated Dec. 29, 2016 (Inventor—Takao Makino; Applicant—Hoya Corporation) (10 pages).

\* cited by examiner

[Fig. 1]
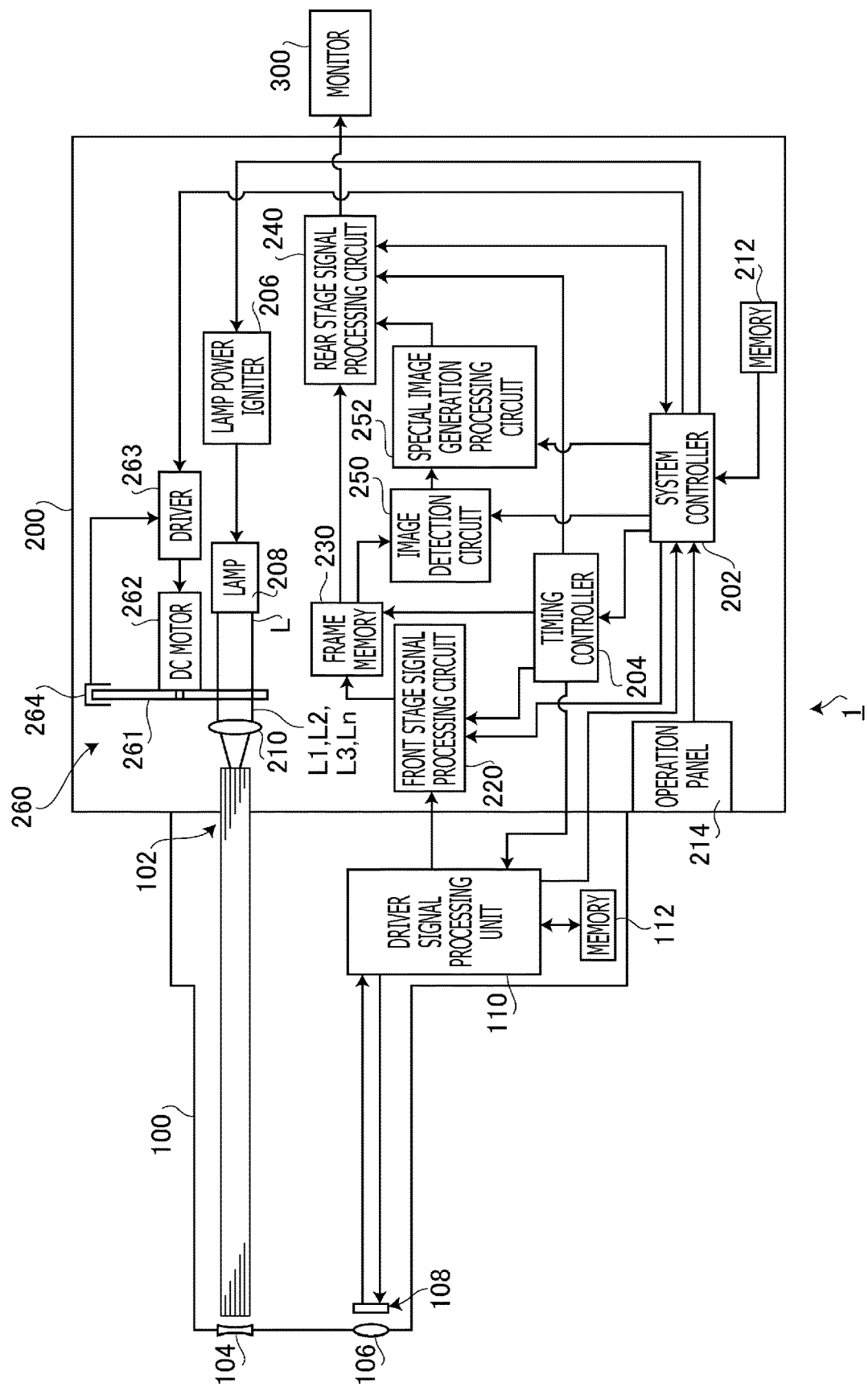

[Fig. 2]
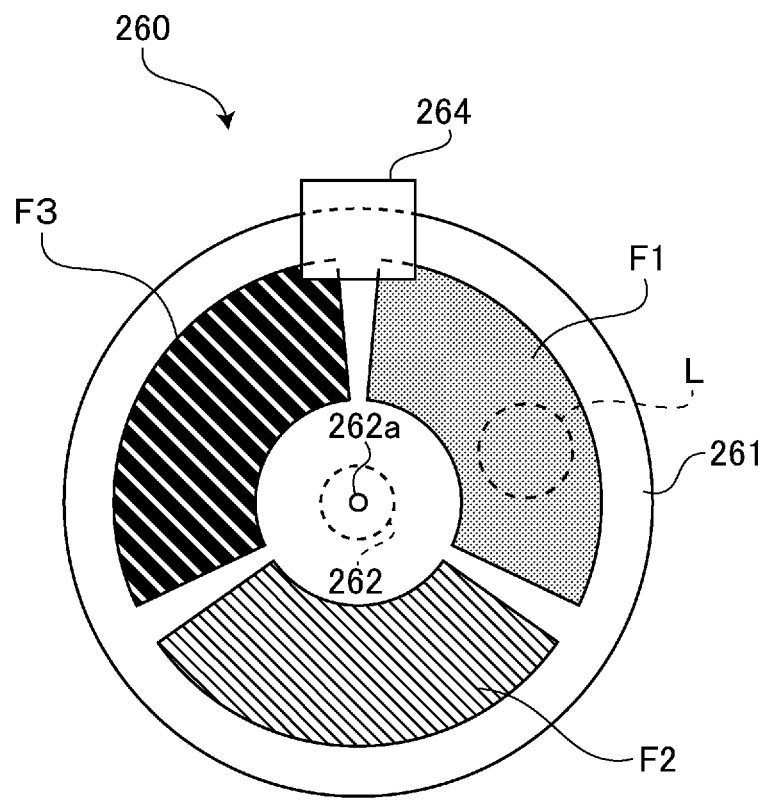

[Fig. 3]
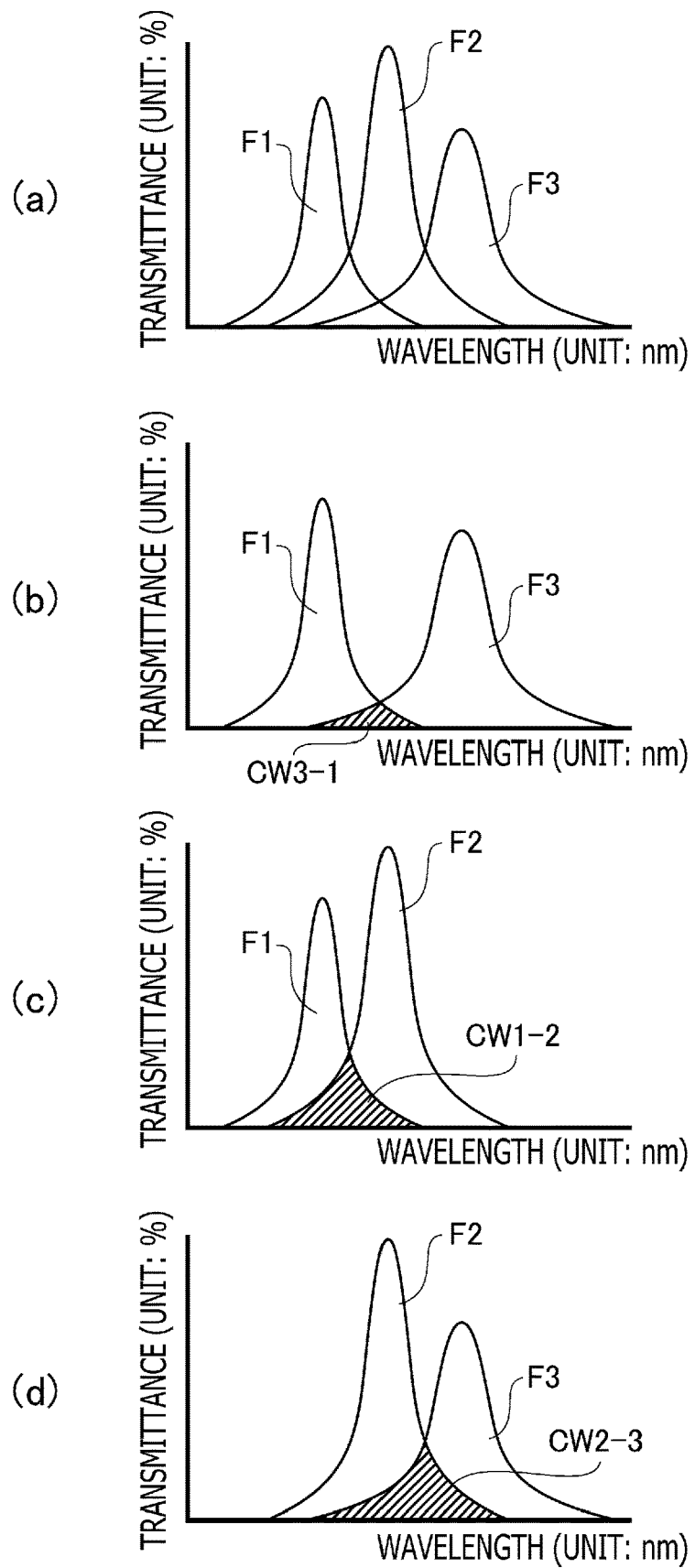

[Fig. 4]
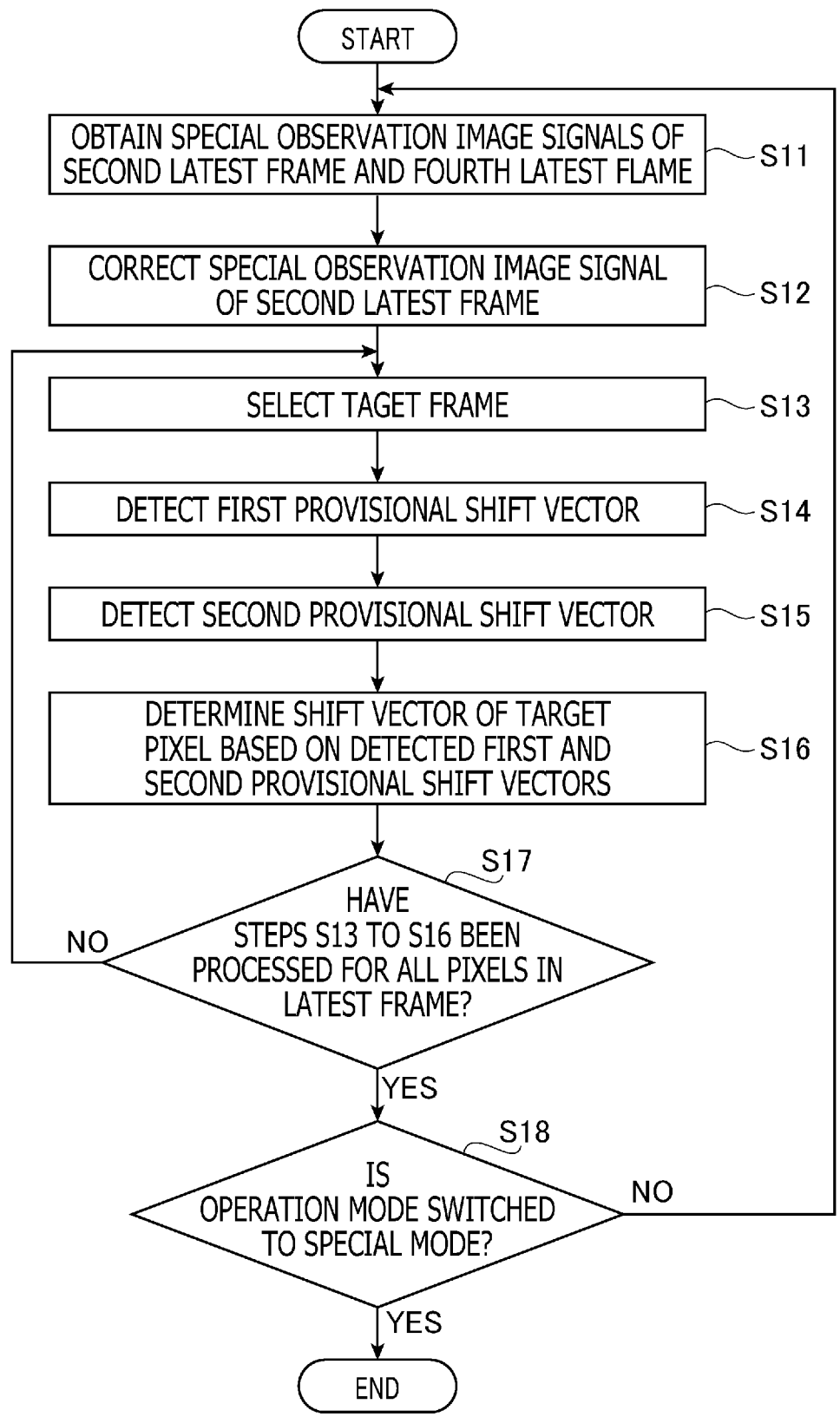

[Fig. 5]
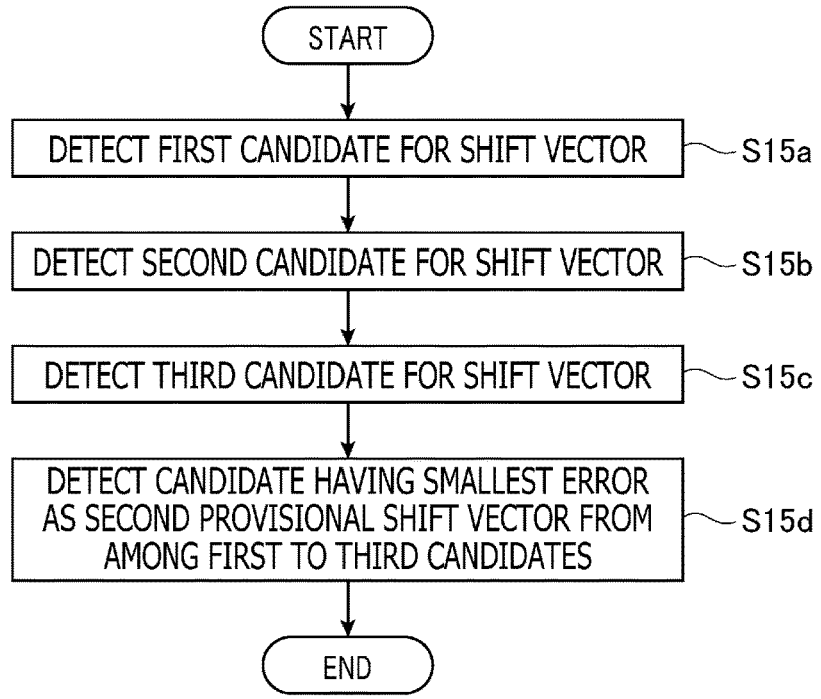
[Fig. 6]
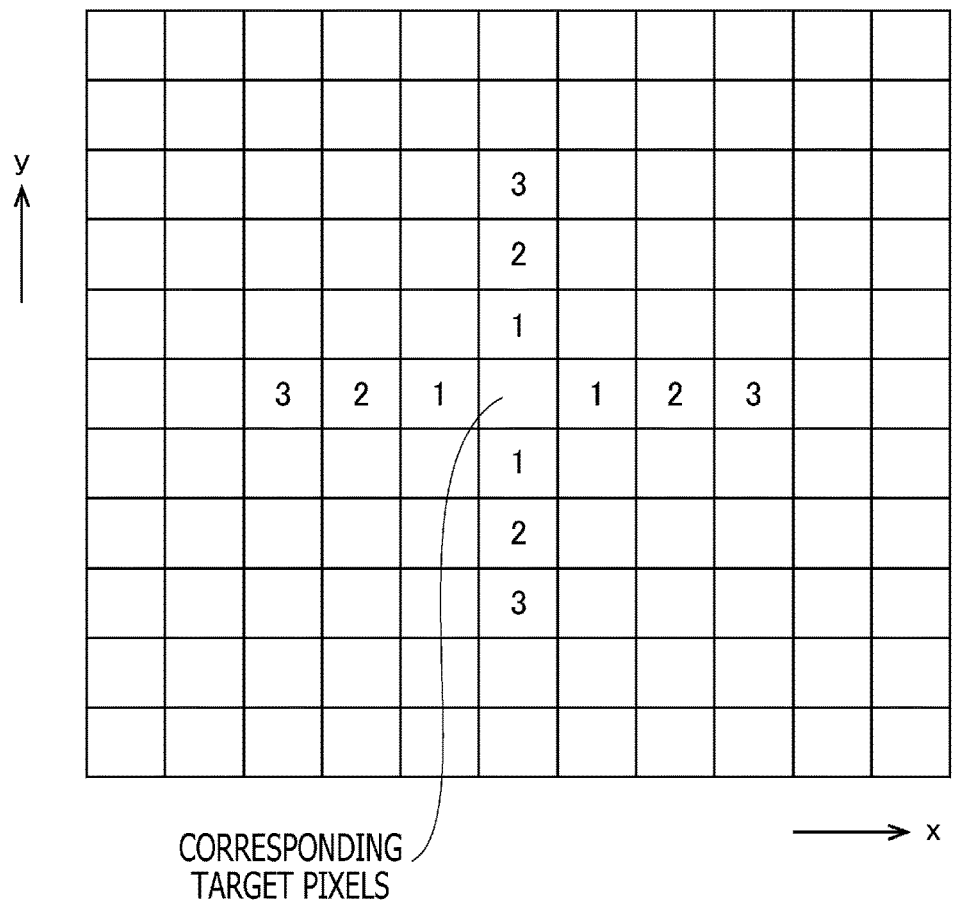
CORRESPONDING TARGET PIXELS

IMAGE DETECTION DEVICE AND IMAGE DETECTION SYSTEM

CROSS-REFERENCE TO RELATED PATENT APPLICATIONS

This application is a U.S. National Phase of International Application No. PCT/JP2016/002655, which was filed Jun. 1, 2016, and which claims the benefit of priority to Japanese Patent Application No. 2015-125968, filed on Jun. 23, 2015. The content of this earlier filed application is hereby incorporated herein by reference in its entirety.

TECHNICAL FIELD

The present invention relates to an image detection device and an image detection system which execute a predetermined detection process for an image.

BACKGROUND ART

A system which executes a predetermined image processing based on a plurality of spectral image data obtained by capturing a subject illuminated with light having different optical properties at timings synchronizing with emission of the light is known. A concrete configuration of a system of this type is described, for example, in International Publication No. WO 2013/047054 A1 (hereafter, referred to as patent document 1).

In the system described in the patent document 1, white light emitted from a light source is sequentially filtered by a spectral filter to become light with narrow bands (each having a band width of approximately 5 nm) of 400, 405, 410, . . . , 800 nm. When a subject, such as a living tissue in a body cavity, is sequentially illuminated with the narrow band light filtered by the spectral filter, the subject is captured by an electronic scope at timings synchronizing with cycles of emission of the narrow band light. Then, using the spectral image data obtained by capturing the subject during emission of the narrow band light, the predetermined image processing is executed. For example, a color image substantially equal to a normal RGB color image is generated using three spectral image data whose center wavelengths are 435 nm, 545 nm and 700 nm, respectively, or a concentration index of oxyhemoglobin is calculated by using three spectral image data whose center wavelengths are 540 nm, 560 nm and 580 nm, respectively. The concentration index of oxyhemoglobin is used for, for example, generation of a color map image according to the concentration of oxyhemoglobin.

In the patent document 1, spectral images corresponding to respective narrow band light are obtained by capturing the subject at timings separated from each other on a time axis. It should be noted that there is no means to fix the electronic scope in the body cavity while the spectral images are captured. Therefore, even if an operator attempts to keep the electronic scope still during capturing of the spectral images, a relative position between the subject and the electronic scope in the body cavity (in other words, a position of the subject in a captured image) shifts. Accordingly, position shift occurs between the spectral images of the subject. For example, since positions of the subject shift with respect to each other between the spectral images of 435 nm, 545 nm and 700 nm, a color shift occurs in a color image of the subject generated by combining these spectral images. Furthermore, since positions of the subject in the spectral images of 540 nm, 560 nm and 580 nm shift with respect to each other, corresponding pixels (pixels having the same address) in the respective spectral images do not show the same portion of the subject. Therefore, an error may be contained in a calculation result of the concentration index of oxyhemoglobin.

In Japanese Patent Provisional Publication No. 2001-136540A (hereafter, referred to as patent document 2), a system which generates an RGB color image by capturing R (red), G (Green) and B (Blue) images through a frame sequential method is described. In the system described in the patent document 2, in order to suppress occurrence of the color shift caused by position shift of a subject in a body cavity, a cross correlation value between the R, G and B images is calculated, a shift vector indicating a relative positional relationship between the images obtained when the cross correlation value becomes the maximum is detected, and the relative position between the images is corrected based on the detected shift vector.

SUMMARY OF INVENTION

It is thought to be possible to suppress occurrence of the color shift caused by the position shift of the subject in the body cavity or to suppress a calculation error of the concentration index of oxyhemoglobin, by applying the configuration described the patent document 2 to the system described in the patent document 1. However, a subject has different reflection properties (sensitivities) for respective wavelength bands of R, G and B. Therefore, in the first place, information on the subject included in the captured image is different between the R, G and B images. Therefore, regarding the method based on the cross correlation between the images described in the patent document 2, it is difficult to detect the shift vector with a high degree of accuracy.

The present invention is made in view of the above described circumstances. That is, the object of the present invention is to provide an image detection device and an image detection system capable of precisely detecting a shift vector between images of a subject illuminated with light having different spectral properties.

According to an aspect of the invention, there is provided an image detection device executing a detection process for images of a subject obtained by illuminating cyclically the subject with light having different spectral properties and capturing the subject at timings synchronizing with illuminating cycles of the light. The image detection device comprises a shift vector detection means that detects a shift vector of the subject based on a comparison result between an image of the subject captured at a current cycle and an image of the subject which is captured at a past cycle and is illuminated with the light having a same spectral property as that of the light illuminated at the current cycle.

Since the shift vector is detected between images illuminated with light having the same spectral property, occurrence of a detection error of the shift vector caused by the difference in spectral property of the light with which the subject is illuminated can be suppressed.

The image detection device may further comprise: a first comparing means that compares a target pixel of the image of the subject captured at the current cycle with a first peripheral pixel which is a pixel of the image of the subject captured at the past cycle and illuminated with the light having the same spectral property of the light at the current cycle, the first peripheral pixel being located in a peripheral portion around a corresponding target pixel which, in the image of the subject captured at the past cycle, corresponds to the target pixel; and a second comparing means that compares the target pixel of the image of the subject captured at the current cycle with a second peripheral pixel which is a pixel of the image of the subject captured at the past cycle and illuminated with the light having the same spectral property of the light at the current cycle, the second peripheral pixel being located in a peripheral part around the corresponding target pixel and located further from the corresponding target pixel relative to the first peripheral pixel. In this configuration, the shift vector detection means detects the shift vector based on comparing results of the first comparing means and the second comparing means.

The first peripheral pixel may adjoin the corresponding target pixel, and the second peripheral pixel may be located to sandwich the first peripheral pixel between the corresponding target pixel and the second peripheral pixel.

The target pixel of the image of the current cycle and the corresponding target pixel of the image of the past cycle have a same address.

The image of the past cycle may be an image captured at preceding emission of the light having a same spectral property as that of the light for the current cycle.

The shift vector detection means may detect a first candidate for the shift vector based on a comparing result by the first comparing means and a second candidate for the shift vector based on a comparing result by the second comparing means. In this case, the shift vector detection means may detect, as the shift vector of the subject, one of the first candidate and the second candidate having a smallest error.

The image detection device may further comprise: a correcting means that corrects an intensity level of an image captured at a preceding cycle preceding the current cycle such that a difference between an intensity level of the image captured at the current cycle and the intensity level of the image captured at the preceding cycle falls with a predetermined tolerance in a common wavelength band which is common to first light emitted when the subject is captured at the current cycle and second light emitted when the subject is captured at the preceding cycle; and a third comparing means that compares the image captured at the current cycle with the image captured at the preceding cycle of which intensity level is corrected by the correcting means. In this configuration, the shift vector detecting means detects the shift vector based on comparing results of the first comparing means, the second comparing means and the third comparing means.

The image detection device may further comprise: a correcting means that corrects an intensity level of an image of a preceding cycle preceding the current cycle such that a difference between an intensity level of the image of the current cycle and the intensity level of the image of the preceding cycle falls with a predetermined tolerance in a common wavelength band which is common to first light emitted when the subject is captured at the current cycle and second light emitted when the subject is captured at the preceding cycle; and a third comparing means that compares the image of the current cycle with the image of the preceding cycle of which intensity level is corrected by the correcting means. In this configuration, the shift vector detecting means obtains a definite value of the shift vector by detecting a provisional value of the shift vector based on a comparing result of the third comparing means and by adding together the detected provisional value of the shift vector and the one of the first candidate and the second candidate having a smallest error while applying predetermined weighting coefficients to the detected provisional value and the one of the first candidate and the second candidate.

The past cycle at which the subject is illuminated with the light having the same spectral property as that of the light for the current cycle may be a cycle prior to the preceding cycle.

According to another aspect of the invention, there is provided an image detection device executing a detection process for images of a subject obtained by illuminating cyclically the subject with light having different wavelength bands and capturing the subject at timings synchronizing with illuminating cycles of the light. The image detection device comprises: a correcting means that corrects an intensity level of an image captured at a preceding cycle preceding the current cycle such that a difference between an intensity level of the image captured at the current cycle and the intensity level of the image captured at the preceding cycle falls with a predetermined tolerance in a common wavelength band which is common to first light emitted when the subject is captured at the current cycle and second light emitted when the subject is captured at the preceding cycle; a comparing means that compares the image captured at the current cycle with the image captured at the preceding cycle corrected by the correcting means; and a shift vector detecting means that detects a shift vector of the subject based on a comparing result by the comparing means.

With this configuration, it is possible to precisely detect a shift vector between images of a subject illuminated with light having different spectral properties.

The image detection device may further comprise a storage means that stores a correction value which has been calculated in advance based on a difference between an intensity level of a captured image captured when the subject having a high degree of sensitivity to the common wavelength band is illuminated with the first light and an intensity level of a captured image captured when the subject is illuminated with the second light. In this configuration, the correcting means corrects the intensity level of the image captured at the preceding cycle by using the correction value stored in the storage unit.

The preceding cycle may be a cycle one cycle before the current cycle.

According to another aspect of the invention, there is provided an image detection system, comprising: a light source device that cyclically emits light having different spectral properties; an image capturing device that captures images of a subject illuminated cyclically with the light having different spectral properties, at timings synchronizing with cycles of emission of the light; and the above described image detection device that executes a detection process for images of the subject captured by the image capturing device.

According to another aspect of the invention, there is provided an image detection system, comprising: a light source device that cyclically emits light having different spectral properties; an image capturing device that captures images of a subject illuminated cyclically with the light having different spectral properties, at timings synchronizing with cycles of emission of the light; and the above described image detection device that executes a detection process for images of the subject captured by the image capturing device. In this configuration, the light emitted by the light source device in cycles adjoining with respect to each other on a time axis has optical properties of including a common wavelength band common to the light in the cycles adjoining with respect to each other.

BRIEF DESCRIPTION OF DRAWINGS

FIG. 1 is a block diagram illustrating an electronic endoscope system according to an embodiment of the invention.

FIG. 2 is a front view of a rotational filter unit viewed from a collecting lens side, according to the embodiment of the invention.

FIG. 3 illustrates examples of spectral properties of a special filter provided in a rotational turret according to the embodiment of the invention.

FIG. 4 is a flowchart illustrating an image detection process executed by an image detection circuit according to the embodiment of the invention.

FIG. 5 is a flowchart illustrating a provisional shift vector detection process executed in step S15 in the image detection process shown in FIG. 4.

FIG. 6 is an explanatory illustration for supplementarily explaining the provisional shift vector detection process.

DESCRIPTION OF EMBODIMENTS

Hereinafter, an embodiment of the present invention is described with reference to the accompanying drawings. In the following explanation, by way of example, an electronic endoscope system is explained as an embodiment of the invention.

(Configuration of Electronic Endoscope System 1)

FIG. 1 is a block diagram illustrating a configuration of an electronic endoscope system 1 according to the embodiment of the invention. As shown in FIG. 1, the electronic endoscope system 1 includes an electronic scope 100, a processor 200 and a monitor 300.

The processor 200 includes a system controller 202 and a timing controller 204. The system controller 202 executes various programs stored in a memory 212, and totally controls the electronic endoscope system 1. Further, the system controller 202 is connected to an operation panel 214. In accordance with an instruction inputted by an operator through the operation panel 214, the system controller 202 alters operation of the electronic endoscope system 1 and parameters for the operation of the electronic endoscope system 1. The instructions inputted by the operator include, for example, an instruction for changing operation modes of the electronic endoscope system 1. In this embodiment, the operation modes include a normal mode and a special mode. The timing controller 204 outputs clock pulses for adjusting timings of the operation to each circuit in the electronic endoscope system 1.

A lamp 208 emits illumination light L after being activated by a lamp power igniter 206. The lamp 208 is, for example, a high intensity lamp, such as a xenon lamp, a halogen lamp, a mercury lamp or a metal-halide lamp, or an LED (Light Emitting Diode). The illumination light L has a spectrum expanding principally from a visible light region to an invisible infrared light region (or white light including at least a visible light region).

FIG. 2 is a front view of a rotational filter unit 206 viewed from a collecting lens 210 side. A rotational filer unit 260 includes a rotational turret 261, a DC motor 262, a driver 263 and a photo-interrupter 264.

The rotational turret 261 is configured to be placed on and retracted from an optical path of the illumination light L by a known mechanism (not shown). More specifically, the rotational turret 261 is retracted from the optical path of the illumination light L when the operation mode of the electronic endoscope system 1 is the normal mode, and is placed on the optical path of the illumination light L when the operation mode of the electronic endoscope system 1 is the special mode. Therefore, in the normal mode, the illumination light L emitted from the lamp 208 is incident on the collecting lens 210 without passing through the rotational turret 261. On the other hand, in the special mode, the illumination light L is incident on the collecting lens 210 while passing through the rotational turret 261.

As shown in FIG. 2, in the rotational turret 261, special light filters F1, F2 and F3 are arranged sequentially in a circumferential direction. Each of the special light filters F1, F2 and F3 has a fan shape. The special light filters F1, F2 and F3 are disposed to have angular pitches corresponding to frame cycles (angular pitches of 120 degrees in this embodiment). Each special light filter is a dielectric multilayer film filter. However, another type of optical filter (e.g., an etalon filter which uses a dielectric multilayer film as a reflection film) may be used as the special light filter. It should be noted that, in the following explanation, the term "frame" may be replaced with the term "field". In this embodiment, the frame cycle and the field cycle are 1/30 seconds and 1/60 seconds, respectively.

Each of the special light filters F1, F2 and F3 is an optical band pass filter which converts the illumination light L inputted from the lamp 208 into light having a particular spectral property. FIGS. 3(a) to 3(d) show examples of the spectral properties of the special light filters F1 to F3. As shown in FIG. 3(a), the special light filters F1 to F3 have different spectral properties. Further, as shown in FIG. 3(b), transmission wavelength bands of the special light filters F1 and F3 partially overlap with each other (i.e., a shaded transmission wavelength band in FIG. 3(b) is common to the special light filters F1 and F3). Furthermore, as shown in FIG. 3(c), transmission wavelength bands of the special light filters F1 and F2 partially overlap with each other (i.e., a shaded transmission wavelength band in FIG. 3(c) is common to the special light filters F1 and F2). Furthermore, as shown in FIG. 3(d), transmission wavelength bands of the special light filters F2 and F3 partially overlap with each other (i.e., a shaded transmission wavelength band in FIG. 3(d) is common to the special light filters F2 and F3).

In the following, for convenience of explanation, the transmission wavelength band common to the special light filters F1 and F3 is referred to as a "common wavelength band CWB3-1", the transmission wavelength band common to the special light filters F1 and F2 is referred to as a "common wavelength band CWB1-2", and the transmission wavelength band common to the special light filters F2 and F3 is referred to as a "common wavelength band CWB2-3". Further, the illumination light L filtered by the special light filter F1 is referred to as "special light L1", the illumination light L filtered by the special light filter F2 is referred to as "special light L2", and the illumination light L filtered by the special light filter F3 is referred to as "special light L3". The illumination light L incident on the collecting lens 210 without passing through the rotational turret 261 is referred to as "normal light Ln".

The driver 263 drives the DC motor 262 under control of the system controller 202. When the DC motor 262 receives a driving current from the driver 263, the DC motor 262 rotates the rotational turret 261 about a motor shaft 262a at a constant speed. By causing the rotational turret 261 to rotate at a constant speed, the special light filters F1, F2 and F3 are sequentially inserted into the optical path of the illumination light L at timings synchronizing with a capturing cycle (a frame cycle). As a result, the special light L1, L2 and L3 having different spectral properties is sequentially extracted, from the illumination light L emitted by the lamp 208, at timings synchronizing with the frame cycle. By repeating rotation of the rotational turret 261, the special light L1, L2 and L3 is cyclically extracted from the illumination light L emitted by the lamp 208. It should be noted that the rotational position and phase of the rotational turret 261 are controlled by detecting a hole (not shown) formed in a peripheral portion of the rotational turret 261 by the photo-interrupter 264.

The illumination light (the normal light Ln or the special light L1, L2 or L3) incident on the collecting lens 210 is converged by the collecting lens 210 and the light amount of the illumination light is limited by a diaphragm (not shown) to an appropriate light amount. Then, the illumination light is converged at an entrance end face of an LCB (Light Carrying Bundle) 102 and enters the LCB 102.

The illumination light (the normal light Ln or the special light L1, L2 or L3) which has entered the LCB 102 propagates through the LCB 102 and emerges from an exit end face of the LCB 102 disposed at a tip of the electronic scope 100. Then, the illumination light is emitted toward a subject (e.g., a living tissue in a body cavity) via a light distribution lens 104. More specifically, in the normal mode, the normal light Ln is emitted toward the subject. In the special mode, the special light L1, L2 and L3 is cyclically emitted toward the subject. Returning light from the subject is converged by an objective lens 106 and thereby an optical image is formed on a light-receiving surface of a solid state image pickup device 108.

The solid state image pickup device 108 is a single chip color CCD (Charge Coupled Device) image sensor having a Bayer type pixel array. The solid state image pickup device 108 accumulates charges according to a light amount of an optical image converged at each pixel on the light-receiving surface, and generates and outputs image signals of R (Red), G (Green) and B (Blue). In the following, the image signal of each pixel (each pixel address) sequentially outputted from the solid state image pickup device 108 is referred to as a "pixel signal". The solid state image pickup device 108 is not limited to a CCD, but may be replaced with a CMOS (Complementary Metal Oxide Semiconductor) image sensor or another type of imaging device. The solid state image pickup device 108 may be a solid state image pickup device of a type mounted with a complementary color filter.

The switching timing of the illumination light (the special light L1, L2 and L3) by the rotational turret 261 is in synchronization with the switching timing of a capturing period (a frame period) in the solid state image pickup device 108. Therefore, in the special mode, the solid state image pickup device 108 outputs a special observation image signal S1 by receiving the returning light from the subject illuminated with the special light L1. In a subsequent frame period, the pickup device 108 outputs a special observation image signal S2 by receiving the returning light from the subject illuminated with the special light L2. In a further subsequent frame period, the pickup device 108 outputs a special observation image signal S3 by receiving the returning light from the subject illuminated with the special light L3. Thus, the special observation image signals S1, S2 and S3 are sequentially generated and outputted by the solid state image pickup device 108. It should be noted that, in the normal mode, the solid state image pickup device 108 generates and outputs a normal observation image signal Sn by receiving the returning light from the subject illuminated with the normal light Ln during each frame period.

In a connection part of the electronic scope 100, a driver signal processing circuit 110 is provided. In the normal mode, the normal observation image signal Sn of the subject illuminated with the normal light Ln is inputted by the solid state image pickup device 108 to the driver signal processing circuit 110 at the frame cycle. In the special mode, the special observation image signals S1, S2 and S3 of the subject illuminated with the special light L1, L2 and L3 are sequentially inputted by the solid state image pickup device 108 to the driver signal processing circuit 110 at the frame cycle. The driver signal processing circuit 110 outputs the image signal inputted from the solid state image pickup device 108, to a front stage signal processing circuit 220 of the processor 200.

Further, the drive signal processing circuit 110 accesses a memory 112 to read unique information of the electronic scope 100. The unique information stored in the memory 112 includes, for example, the pixel number and sensitivity of the solid state image pickup device 108, available frame rates, and a model number. The driver signal processing circuit 100 outputs the unique information read from the memory 112 to the system controller 202.

The system controller 202 executes various computations based on the unique information of the electronic scope 100 and generates control signals. Using the generated control signals, the system controller 202 controls operation and timings of various circuits in the processor 200 so that appropriate processing is performed for an electronic scope connected to the processor 200.

In accordance with the timing control by the system controller 202, the timing controller 204 supplies the driver signal processing circuit 110 with clock pulses. In accordance with the clock pulses supplied from the timing controller 204, the driver signal processing circuit 110 drives and controls the solid state image pickup device 108 at timings synchronizing with the frame rate of a video being processed on the processor 200 side.

(Operation in Normal Mode)

Signal processing operation of the processor 200 in the normal mode will now be explained.

The front stage signal processing circuit 200 subjects the normal observation image signal Sn to predetermined signal processing, such as demosaicing, a matrix operation, white balance adjustment and gamma correction, to generate image data suitable for onscreen representation. The generated image data is inputted to a rear stage signal processing circuit 240 via a frame memory 230.

The rear stage signal processing circuit 240 subjects the image data inputted from the frame memory 230 to predetermined signal processing to generate image data for monitor representation, and converts the image data for monitor representation into a predetermined video format signal. The converted video format signal is outputted to the monitor 300. As a result, a normal color image of the subject is displayed on a display screen of the monitor 300.

(Operation in Special Mode)

Signal processing operation of the processor 200 in the special mode will now be explained.

The front stage signal processing circuit 200 subjects the special observation image signals S1 to S3 to predetermined signal processing, such as demosaicing, a matrix operation, white balance adjustment and gamma correction, and outputs the signals to the frame memory 230. In the frame memory 230, latest four frames of the special observation image signals (the current frame, the immediately preceding frame of the current frame, the frame two frames earlier than the current frame, and the frame three frames earlier than the current frame) are sequentially written and stored in the frame memory 230. In the following, for convenience of explanation, the current frame, the immediately preceding frame of the current frame, the frame two frames earlier than the current frame, the frame three frames earlier than the current frame are referred to as a "latest frame", a "second latest frame", a "third latest frame" and a "fourth latest frame", respectively.

(Image Detection Process)

FIG. 4 is a flowchart illustrating an image detection process executed by an image detection circuit 250 provided in the processor 200. The image detection process shown in FIG. 4 is started when the operation mode of the electronic endoscope system 1 is switched to the special mode.

(S11 in FIG. 4 (Obtaining of Special Observation Image Signal of Each Frame))

In step S11, the special observation image signals of the second latest frame and the fourth latest frame stored in the frame memory 230 are obtained.

(S12 in FIG. 4 (Correction of Special Observation Image Signal of Second Latest Frame))

In the memory 212, first to third correction values have been stored in advance. The first correction value has been calculated in advance based on the difference between intensity levels of the special observation image signals S1 and S3 obtained when a specific subject having a high sensitivity to the common wavelength band CWB3-1 is captured, such that the difference between the intensity levels of these special observation image signals S1 and S3 falls within a predetermined tolerance. The second correction value has been calculated in advance based on the difference between intensity levels of the special observation image signals S1 and S2 obtained when a specific subject having a high sensitivity to the common wavelength band CWB1-2 is captured, such that the difference between the intensity levels of these special observation image signals S1 and S2 falls within a predetermined tolerance. The third correction value has been calculated in advance based on the difference between intensity levels of the special observation image signals S2 and S3 obtained when a specific subject having a high sensitivity to the common wavelength band CWB2-3 is captured, such that the difference between these intensity levels of the special observation image signals S2 and S3 falls within a predetermined tolerance.

In step S12, a corresponding correction value is read from the first to third correction values stored in the memory 212, and the intensity level of the special observation image signal of the second latest frame is corrected. Specifically, when the latest frame is a captured frame of a subject illuminated with the special light L1, the first correction value is read from the memory 212, and the intensity level of the special observation image signal S3 of the second latest frame is corrected. When the latest frame is a captured frame of a subject illuminated with the special light L2, the second correction value is read from the memory 212, and the intensity level of the special observation image signal S1 of the second latest frame is corrected. When the latest frame is a captured frame of a subject illuminated with the special light L3, the third correction value is read from the memory 212, and the intensity level of the special observation image signal S2 of the second latest frame is corrected.

That is, in step S12, by executing the correction process using the correction value according to the difference between the intensity levels of the latest frame and the second latest frame in the common wavelength band, the difference between the intensity levels of the latest frame and the second latest frame (i.e., the difference of subject information) due to the difference of the capturing condition (the difference of spectral properties in this embodiment) is reduced.

(S13 in FIG. 4 (Selection of Target Pixel))

In step S13, a target pixel is selected, in accordance with predetermined order, from among all the pixels in the latest frame inputted from the front stage signal processing circuit 220. Furthermore, a corresponding target pixel is selected from among all the pixels of the special observation image signal of each of the second latest frame and the fourth latest frame. The target pixel and the corresponding target pixels are, for example, pixels having the same address.

(S14 in FIG. 4 (Detection of First Provisional Shift Vector))

In step S14, corresponding target pixel data of the special observation image signal of the second latest frame corrected in step S12 (correction of special observation image signal of latest frame) is compared with target pixel data of the special observation image signal of the latest frame to detect a provisional shift vector (a first provisional shift vector) of the target pixel.

In this embodiment, a shift vector is a parameter indicating motion (a direction and an amount) per a unit time of a subject in a captured image. The shift vector is estimated using the gradient-based method (the optical flow) having a low degree of processing load to realize real-time detection. In the gradient-based method, when a gradient of a pixel value with respect to a neighboring pixel in the horizontal (x) direction is defined as Ix, a gradient of a pixel value with respect to a neighboring pixel in the vertical direction (y) is defined as Iy, a gradient of a pixel value in the time-axis direction is defined as It, and the shift vector is defined as (u, v), the shift vector is calculated by the following expression.

$$Ix \cdot u + Iy \cdot v + It = 0$$

In place of the gradient-based method, another type of known estimation technique, such as the block matching method or an estimation process based on frequency analysis of a captured image, may be used to estimate the shift vector.

(S15 in FIG. 4 (Detection of Second Provisional Shift Vector))

In step S15, two frames having the same spectral property of the special light with which the subject is illuminated are compared with each other (specifically, image data of the special observation image signal of the latest frame and image data of the special observation image signal of the fourth latest frame are compared with each other) to detect a provisional shift vector (a second provisional shift vector). As an example, when the latest frame is a captured frame of a subject illuminated with the special light L1, the fourth latest frame is also a captured frame of the subject illuminated with the special light L1. In this case, image data of the special observation image signals S1 of the latest frame and the fourth latest frame are compared with each other to detect the second provisional shift vector.

That is, since, in step S15, two pieces of image data having the same capturing condition (special property of the illumination light in this embodiment) are compared with each other, the second provisional shift vector is detected in a state where an error due to the difference in the capturing condition (in other words, the difference in subject information) is excluded.

FIG. 5 is a flowchart illustrating a provisional shift vector detection process executed in step S15. FIG. 6 is an explanatory illustration for supplementarily explaining the provisional shift vector detection process.

(S15*a* in FIG. 5)

In step S15*a*, using the target pixel data of the latest frame and image data of first peripheral pixels (pixels assigned a reference symbol "1" in FIG. 6) adjoining the corresponding target pixel of the fourth latest frame in the horizontal and vertical directions (x, y), a candidate for the second provisional shift vector (hereafter referred to as a "first candidate" for convenience of explanation) is detected in accordance with the gradient-based method.

(S15*b* in FIG. 5)

In step S15*b*, using the target pixel data of the latest frame and image data of second peripheral pixels (pixels assigned a reference symbol "2" in FIG. 6) positioned to sandwich the first peripheral pixels in the horizontal and vertical directions (x, y) with respect to the corresponding target pixel of the fourth latest frame, a candidate for the second provisional shift vector (hereafter referred to as a "second candidate" for convenience of explanation) is detected in accordance with the gradient-based method.

(S15*c* in FIG. 5)

In step S15*c*, using the target pixel data of the latest frame and image data of third peripheral pixels (pixels assigned a reference symbol "3" in FIG. 6) positioned to sandwich the first and second peripheral pixels in the horizontal and vertical directions (x, y) with respect to the corresponding target pixel of the fourth latest frame, a candidate for the second provisional shift vector (hereafter referred to as a "third candidate" for convenience of explanation) is detected in accordance with the gradient-based method.

(S15*d* in FIG. 5)

Since, in the gradient-based method, time differentiation and spatial differentiation of the image intensity are calculated, it becomes possible to more precisely detect the shift vector as the time and spatial sampling frequency becomes higher. In other words, in order to detect the shift vector with a high degree of precision, it is necessary to make the sampling frequency higher for both of the time and the space.

When at least one of the sampling frequencies for the time and the space is low, there is a possibility that the shift vector to be detected contains a large error. Let us consider, for example, a case where the sampling frequency for the space is high and the sampling frequency for the time is low. In this case, when the moving amount of a subject is small, a detection error of the shift vector is small. However, when the moving amount of the subject is large, the detection error becomes large. In order to suppress this sort of detection error, it is thought to be suitable to set the sampling frequency of the space to be low (coarse) in accordance with the motion amount of the subject.

For this reason, when the sampling frequency of the time is low (when detection of the shift vector is performed by using the two frames having an interval of three frames (i.e., the latest frame and the fourth latest frame)), the sampling frequency for the space is set to be high (corresponding to one pixel pitch) in step S15*a*, the sampling frequency for the space is set to be middle (corresponding to two pixel pitch) in step S15*b*, and the sampling frequency for the space is set to be low (corresponding to three pixels) in step S15*c*. That is, in this embodiment, the second provisional shift vector is detected assuming the case where the moving amount of the subject is small, the case where the moving amount is middle and the case where the moving amount of the subject is large.

In step S15*d*, a candidate of which error is the minimum is selected as the second provisional shift vector from among the first to third candidates.

(S16 in FIG. 4 (Determination of Shift Vector))

By adding together the first provisional shift vector detected in step S14 (detection of first provisional shift vector) and the second provisional shift vector detected in step S15 (detection of second provisional shift vector) while applying predetermined coefficients for weighting to these provisional shift vectors, a definite value of the shift vector is determined for the target pixel. The coefficients for weighting may be set in advance or may be set through a user operation.

(S17 in FIG. 14 (Judgment on Completion of Execution of Process for All Pixels))

In step S17, it is judged whether steps S13 to S16 have been executed for all the pixels of the latest frame.

When there is a pixel for which steps S13 to S16 have not been processed (S17: NO), the image detection process shown in FIG. 4 returns to step S13 (selection of target process) to execute steps S13 to S1 for the next target pixel.

(S18 in FIG. 4 (Termination Judgment))

Step S18 is executed when it judged in step S17 that steps S13 to S16 have been processed for all the pixels of the latest frame in step S17 (judgment on completion of execution of process for all pixels) (S17: YES). In step S18, it is judged whether the operation mode of the electronic endoscope system 1 has been switched to a mode different from the special mode. When it is judged that the operation mode has not been switched to a mode different from the special mode (S18: NO), the image detection process in FIG. 4 returns to step S1 (obtaining of special observation image signal of each frame). On the other hand, when it is judged that the operation mode has been switched to a mode different from the special mode (S18: YES), the image detection process in FIG. 4 is terminated.

(Generation and Representation of Image in Special Mode)

A special image generation processing circuit 252 corrects a relative positional relationship between captured images of the subject illuminated with the special light L1 to L3 based on the shift vector detected by the image detection process in FIG. 4 (step S16 in FIG. 4 (determination of shift vector)). Let us consider, for example, a case where the shift vector between the latest frame and the second latest frame is one pixel in the horizontal direction (the rightward direction) and the shift vector between the second latest frame and the third latest frame is two pixels in the horizontal direction (the rightward direction). In this case, a pixel (x, y) of the latest frame is corrected by adding together a pixel (x, y) of the latest frame, a pixel (x-1, y) of the second latest frame and a pixel (x-3, y) of the third latest frame while applying predetermined weighting coefficients.

Next, the special image generation processing circuit 252 executes, for example, generating pixel data of a color image in which the corrected captured images are combined or a special image (e.g., an image for highlighting a particular portion), or calculating a concentration index of oxyhemoglobin and generating pixel data of a color map image of oxyhemoglobin concentration based on a result of the calculation.

The pixel data generated by the special image generation processing circuit 252 is inputted to the rear stage signal processing circuit 240. The rear stage signal processing circuit 240 subjects the pixel data inputted from the special image generation processing circuit 252 to predetermined signal processing to generate image data for monitor representation, and converts the generated image data for monitor representation into a predetermined video format signal. The converted video format signal is outputted to the monitor 300. As a result, a color image or a special image of the subject, and a color map image of oxyhemoglobin concentration are displayed on the display screen of the monitor 300.

As described above, according to the embodiment, the shift vector is detected (see S14 in FIG. 4 (detection of first provisional shift vector)) in a state where the difference in intensity level due to the difference in spectral property of the special light is corrected (see S12 in FIG. 4 (correction of special observation image signal of latest frame)). Furthermore, the shift vector is detected between the frames having the same spectral property of the special light (S15 in FIG. 4 (detection of second provisional shift vector)). That is, since the shift vector is detected in a state where the difference in capturing conditions is excluded as much as possible, the detection accuracy of the shift vector is enhanced.

The foregoing is the explanation about the embodiment of the invention. The invention is not limited to the above described embodiment, but can be varied in various ways within the scope of the invention. For example, the invention includes a combination of embodiments explicitly described in this specification and embodiments easily realized from the above described embodiment.

In the above described embodiment, the shift vector of the target pixel is detected based on both of the first provisional shift vector detected in step S14 (detection of first provisional shift vector) and the second provisional shift vector detected in step S15 (detection of second provisional shift vector); however, the present invention is not limited to such a configuration. In another embodiment, the first provisional shift vector may be employed as a definite value of the shift vector (i.e., the second provisional shift vector may not be detected) or the second provisional shift vector may be employed as a definite value of the shift vector (i.e., the first provisional shift vector may not be detected).

The invention claimed is:

1. An image detection device configured to execute a detection process for images of a subject obtained by illuminating cyclically the subject with light having different spectral properties and capturing the subject at timings synchronizing with illuminating cycles of the light, the image detection device comprising:
a first comparator configured to compare a target pixel of an image of the subject captured at a current cycle with a first peripheral pixel of an image of the subject captured at a past cycle and illuminated with light having a same spectral property as light that illuminates the subject at the current cycle, the first peripheral pixel being located in a peripheral portion around a corresponding target pixel which, in the image of the subject captured at the past cycle, corresponds to the target pixel;
a second comparator configured to compare the target pixel of the image captured at the current cycle with a second peripheral pixel of the image captured at the past cycle, the second peripheral pixel being located in a peripheral part around the corresponding target pixel and being located further from the corresponding target pixel than the first peripheral pixel is; and
a shift vector detector configured to detect a first candidate based on a comparing result of the first comparator and a second candidate based on a comparing result of the second comparator,
wherein the shift vector detector is configured to detect a shift vector of the subject based on an error of the first candidate and an error of the second candidate.

2. The image detection device according to claim 1, wherein:
the first peripheral pixel adjoins the corresponding target pixel; and
the second peripheral pixel is located to sandwich the first peripheral pixel between the corresponding target pixel and the second peripheral pixel.

3. The image detection device according to claim 1, wherein the target pixel of the image of the current cycle and the corresponding target pixel of the image of the past cycle have a same address.

4. The image detection device according to claim 1, wherein the image of the past cycle is an image captured at a preceding emission of light having the same spectral property as light that illuminates the subject at the current cycle.

5. The image detection device according to claim 1, wherein the shift vector detector is configured to detect, as the shift vector of the subject, one of the first candidate and the second candidate having a smallest error.

6. The image detection device according to claim 1, further comprising:
a corrector configured to correct an intensity level of an image of the subject captured at a cycle preceding the current cycle and illuminated with light having a different spectral property than light that illuminates the subject at the current cycle such that a difference between an intensity level of the image captured at the current cycle and the intensity level of the image captured at the preceding cycle falls within a predetermined tolerance in a common wavelength band which is common to light that illuminates the subject at the current cycle and light that illuminates the subject at the preceding cycle; and
a third comparator configured to compare the image captured at the current cycle with the image captured at the preceding cycle of which intensity level is corrected by the corrector,
wherein the shift vector detector is configured to detect the shift vector based on the comparing result of the first comparator, the comparing result of the second comparator, and a comparing result of the third comparator.

7. The image detection device according to claim 6, wherein the shift vector detector is configured to obtain a definite value of the shift vector by detecting a provisional value of the shift vector based on the comparing result of the third comparator and by adding together the detected provisional value of the shift vector and the one of the first candidate and the second candidate having a smallest error while applying predetermined weighting coefficients to the detected provisional value and the one of the first candidate and the second candidate.

8. The image detection device according to claim 6, further comprising a storage configured to store a correction value which has been calculated in advance based on a difference between an intensity level of a captured image captured when a subject having a high degree of sensitivity to the common wavelength band is illuminated with light having the same spectral property as light that illuminates the subject at the current cycle and an intensity level of a captured image captured when the subject having a high degree of sensitivity to the common wavelength band is illuminated with light having the different spectral property than light that illuminates the subject at the current cycle,
  wherein the corrector is configured to correct the intensity level of the image captured at the preceding cycle by using the correction value stored in the storage.

9. The image detection device according to claim 6, wherein the preceding cycle is a cycle one cycle before the current cycle.

10. The image detection device according to claim 1, wherein the shift vector indicates a direction and an amount of motion of the subject.

11. The image detection device according to claim 1, wherein the spectral property of light that illuminates the subject at the current cycle is a first wavelength band, and
  wherein light that illuminates the subject at a cycle that adjoins the current cycle on a time axis has a different spectral property than light that illuminates the subject at the current cycle, and
  wherein the different spectral property is a second wavelength band that partially overlaps the first wavelength band, the second wavelength band having a center wavelength that is different than a center wavelength of the first wavelength band.

12. An image detection system, comprising:
  a light source device configured to cyclically emit light having different spectral properties;
  an image capturing device configured to capture images of a subject illuminated cyclically with the light having different spectral properties, at timings synchronizing with cycles of emission of the light; and
  an image detection device comprising:
  a first comparator configured to compare a target pixel of an image of the subject captured at a current cycle with a first peripheral pixel of an image of the subject captured at a past cycle and illuminated with light having a same spectral property as light that illuminates the subject at the current cycle, the first peripheral pixel being located in a peripheral portion around a corresponding target pixel which, in the image of the subject captured at the past cycle, corresponds to the target pixel;
  a second comparator configured to compare the target pixel of the image captured at the current cycle with a second peripheral pixel of the image captured at the past cycle, the second peripheral pixel being located in a peripheral part around the corresponding target pixel and being located further from the corresponding target pixel than the first peripheral pixel is; and
  a shift vector detector configured to detect a first candidate based on a comparing result of the first comparator and a second candidate based on a comparing result of the second comparator,
  wherein the shift vector detector is configured to detect a shift vector of the subject based on an error of the first candidate and an error of the second candidate.

13. The image detection system according to claim 12, further comprising:
  a corrector configured to correct an intensity level of an image of the subject captured at a cycle preceding the current cycle and illuminated with light having a different spectral property than light illuminating the subject at the current cycle such that a difference between an intensity level of the image captured at the current cycle and the intensity level of the image captured at the preceding cycle falls within a predetermined tolerance in a common wavelength band which is common to light that illuminates the subject at the current cycle and light that illuminates the subject at the preceding cycle; and
  a third comparator configured to produce a result of comparing the image captured at the current cycle with the image captured at the preceding cycle of which intensity level is corrected by the corrector,
  wherein the shift vector detector is configured to detect the shift vector based on the results produced by the first comparator, the second comparator and the third comparator.

14. The image detection system according to claim 13, further comprising a storage configured to store a correction value which has been calculated in advance based on a difference between an intensity level of a captured image captured when a subject having a high degree of sensitivity to the common wavelength band is illuminated with light having the same spectral property as light that illuminates the subject at the current cycle and an intensity level of a captured image captured when the subject having a high degree of sensitivity to the common wavelength band is illuminated with light having the different spectral property than light illuminating the subject at the current cycle,
  wherein the corrector is configured to correct the intensity level of the image captured at the preceding cycle by using the correction value stored in the storage.

15. The image detection system according to claim 12, wherein the shift vector indicates a direction and an amount of motion of the subject.

16. The image detection system according to claim 12, wherein the spectral property of light that illuminates the subject at the current cycle is a first wavelength band, and
  wherein light that illuminates the subject at a cycle that adjoins the current cycle on a time axis has a different spectral property than light that illuminates the subject at the current cycle, and
  wherein the different spectral property is a second wavelength band that partially overlaps the first wavelength band, the second wavelength band having a center wavelength that is different than a center wavelength of the first wavelength band.

17. A detection process comprising:
  capturing images of a subject illuminated cyclically with light having different spectral properties, at timings synchronizing with cycles of emission of the light; and
  comparing a target pixel of an image of the subject captured at a current cycle with a first peripheral pixel of an image of the subject captured at a past cycle and illuminated with light having a same spectral property as light that illuminates the subject at the current cycle, the first peripheral pixel being located in a peripheral portion around a corresponding target pixel which, in the image of the subject captured at the past cycle, corresponds to the target pixel;
  comparing the target pixel of the image captured at the current cycle with a second peripheral pixel of the image captured at the past cycle, the second peripheral pixel being located in a peripheral part around the corresponding target pixel and being located further from the corresponding target pixel than the first peripheral pixel is;
  detecting a first candidate based on a result of the comparing the target pixel with the first peripheral pixel and a second candidate based on a result of the comparing the target pixel with the second peripheral pixel; and detecting a shift vector of the subject based on an error of the first candidate and an error of the second candidate.

18. The detection process according to claim 17, further comprising:

correcting an intensity level of an image of the subject captured at a cycle preceding the current cycle and illuminated with light having a different spectral property than light that illuminates the subject at the current cycle such that a difference between an intensity level of the image captured at the current cycle and the intensity level of the image captured at the preceding cycle falls within a predetermined tolerance in a common wavelength band, the common wavelength band being common to light that illuminates the subject at the current cycle and light that illuminates the subject at the preceding cycle; and comparing the image captured at the current cycle with the image captured at the preceding cycle of which intensity level is corrected by the correcting, wherein the detecting the shift vector is based on the result of comparing the target pixel with the first peripheral pixel, the result of comparing the target pixel with the second peripheral pixel, and a result of the comparing the image captured at the current cycle with the image captured at the preceding cycle.

19. The detection process according to claim 17, wherein the shift vector indicates a direction and an amount of motion of the subject.

20. The detection process according to claim 17, wherein the spectral property of light that illuminates the subject at the current cycle is a first wavelength band, and wherein light that illuminates the subject at a cycle that adjoins the current cycle on a time axis has a different spectral property than light that illuminates the subject at the current cycle, and wherein the different spectral property is a second wavelength band that partially overlaps the first wavelength band, the second wavelength band having a center wavelength that is different than a center wavelength of the first wavelength band.

\* \* \* \* \*